(12) United States Patent
Struble

(10) Patent No.: US 6,609,028 B2
(45) Date of Patent: Aug. 19, 2003

(54) PVC RESPONSE-TRIGGERED BLANKING IN A CARDIAC PACING SYSTEM

(75) Inventor: Chester Struble, Eijsden (NL)

(73) Assignee: Medtronic, Inc., Minneapolis, MN (US)

(*) Notice: Subject to any disclaimer, the term of this patent is extended or adjusted under 35 U.S.C. 154(b) by 285 days.

(21) Appl. No.: 09/842,232

(22) Filed: Apr. 26, 2001

(65) Prior Publication Data

US 2002/0183792 A1 Dec. 5, 2002

(51) Int. Cl.$^7$ ............................................. A61N 1/368
(52) U.S. Cl. ............................................ 607/14; 607/9
(58) Field of Search ................................ 607/9, 14, 15

(56) References Cited

U.S. PATENT DOCUMENTS

| | | |
|---|---|---|
| 3,937,226 A | 2/1976 | Funke |
| 4,088,140 A | 5/1978 | Rockland et al. |
| 4,316,472 A | 2/1982 | Mirowski et al. |
| 4,354,497 A | 10/1982 | Kahn |
| 4,375,817 A | 3/1983 | Engle et al. |
| 4,384,585 A | 5/1983 | Zipes |
| 4,476,868 A | 10/1984 | Thompson |
| 4,556,063 A | 12/1985 | Thompson et al. |
| 4,587,970 A | 5/1986 | Holley et al. |
| 4,726,380 A | 2/1988 | Vollmann et al. |
| 4,727,877 A | 3/1988 | Kallok |
| 4,788,980 A * | 12/1988 | Mann et al. ................... 607/14 |
| 4,800,883 A | 1/1989 | Winstrom |
| 4,880,005 A | 11/1989 | Pless et al. |
| 4,928,688 A | 5/1990 | Mower |
| 4,949,719 A | 8/1990 | Pless et al. |
| 4,953,551 A | 9/1990 | Mehra et al. |
| 5,099,838 A | 3/1992 | Bardy |
| 5,117,824 A | 6/1992 | Keimel et al. |
| 5,131,388 A | 7/1992 | Pless et al. |
| 5,144,949 A | 9/1992 | Olson |
| 5,158,078 A | 10/1992 | Bennett et al. |
| 5,188,105 A | 2/1993 | Keimel |
| 5,199,428 A | 4/1993 | Obel et al. |
| 5,269,298 A | 12/1993 | Adams et al. |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennett et al. |
| 5,388,586 A | 2/1995 | Lee et al. |
| 5,545,186 A | 8/1996 | Olson et al. |
| 5,683,429 A | 11/1997 | Mehra |
| 6,311,088 B1 * | 10/2001 | Betzold et al. ................ 607/14 |

OTHER PUBLICATIONS

"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp 167–170.

* cited by examiner

*Primary Examiner*—Kennedy Schaetzle
(74) *Attorney, Agent, or Firm*—Thomas F. Woods; Eric R. Woldkoetter; Tom G. Berry

(57) ABSTRACT

A biventricular pacing system incorporates a premature ventricular contraction (PVC) response. The biventricular pacing system also includes a programmable ventricular blanking period (VBP) that is initiated with the PVC response. During the programmed VBP, ventricular events are effectively blanked out. This prevents both ventricular leads from each independently initiating a dual PVC response, based on the same PVC event.

65 Claims, 8 Drawing Sheets

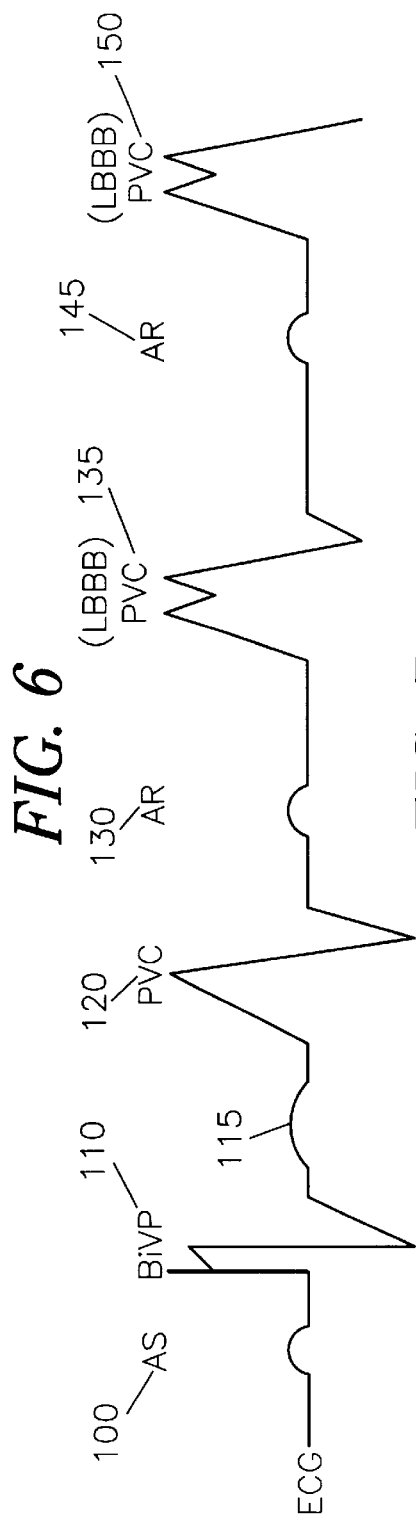
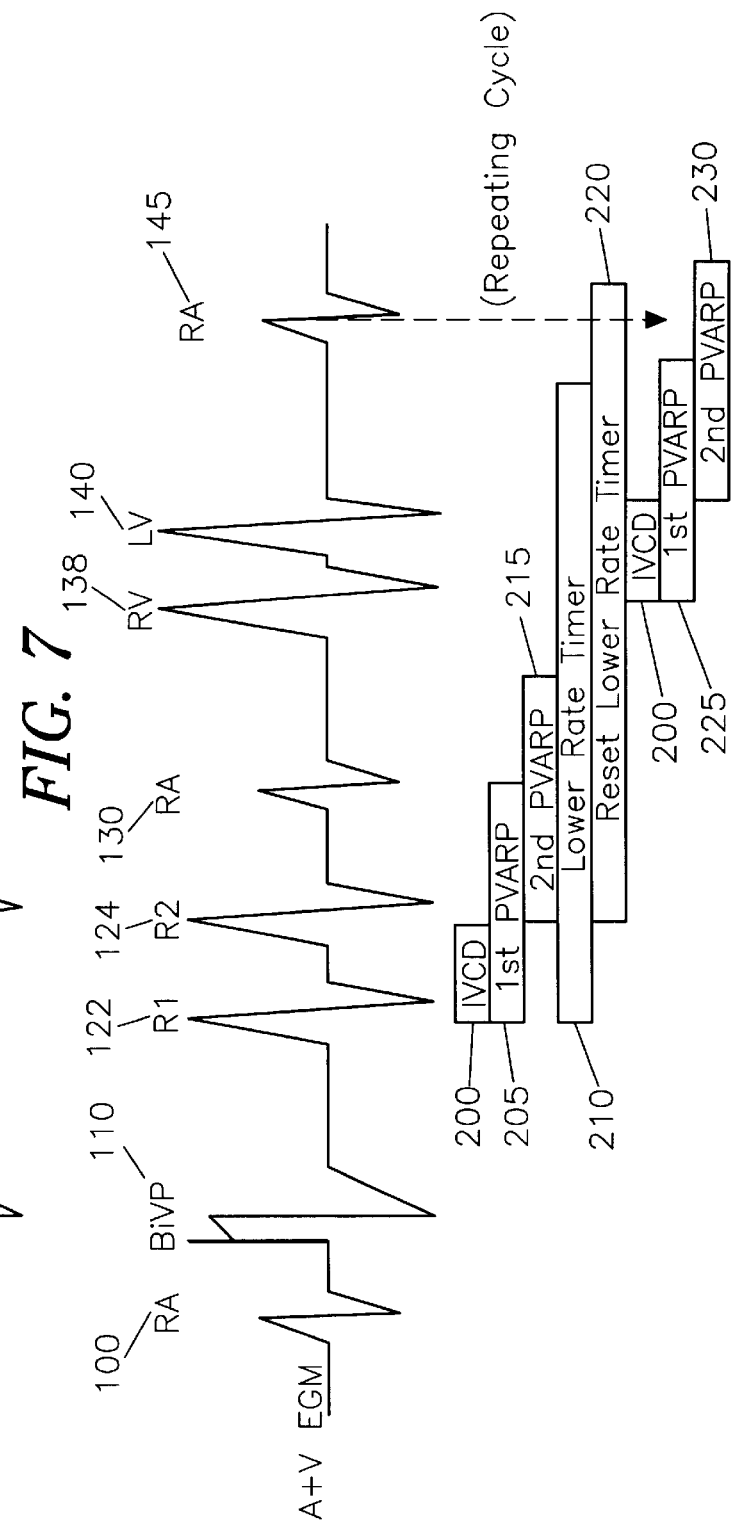

PVC RESPONSE-TRIGGERED BLANKING IN A CARDIAC PACING SYSTEM

FIELD OF THE INVENTION

The present invention generally relates to implantable cardiac pacemakers. More specifically, the present invention relates to the sensing parameters of biatrial and/or biventricular pacing systems.

BACKGROUND

Modern implantable pacemakers are provided in various configurations to provide particular therapies. Certain variations of these pacemakers sense and/or pace within two, three or four chambers of the heart. Early pacemakers generally included a single atrial lead and/or a single ventricular lead, thus limiting both sensing and pacing functions. More recently, pacemakers have been utilized having biatrial and/or biventricular lead configurations. Thus, pacing and sensing can be targeted to more specific areas within the heart.

One type of cardiac event handled by implantable pacemakers is the premature ventricular contraction (PVC). A PVC can generally be identified by a pacing system as a ventricular sensed event that follows another ventricular event without an intervening atrial event.

Once a PVC has been identified, various pacing systems will react to the event. One type of PVC response is the initiation of an extended post-ventricular atrial refractory period (PVARP) of 400 ms. An extended PVARP is a predetermined time window, during which atrial events are ignored or "blanked" out. This is a preventative mechanism to avoid detecting retrograde P waves within the atrial chambers and inadvertently triggering a pacemaker mediated tachycardia (PMT).

The use of an extended PVARP within the programming of an implantable pacemaker is an effective safety mechanism to avoid PMT. However, with the advent of biventricular pacing and sensing, a new problem arises in that the dual sensing of the same ventricular event will retrigger the initiation of the extended PVARP. Thus, instead of having a window of 400 ms, the extended PVARP is effectively extended by the length of the interventricular conduction delay (IVCD), which is usually between 80–180 ms. This makes the "total" extended PVARP too long in that intrinsic conduction will occur within the heart and be misclassified as a PVC. This will become a repetitive cycle known as extended ventricular sensing.

To avoid this condition, implantable pacemakers having biventricular sensing capabilities have been programmed so as to disable the extended PVARP function. This does effectively avoid the initiation of extended ventricular sensing. It also means that a useful safety feature, namely the PVC response function, is bypassed and unused. This is undesirable in that pacemaker mediated tachycardia becomes possible.

Table 1 lists patents that disclose pacemakers that provide biatrial and biventricular pacing. Typically, these references fail to address the issues arising from the use of an extended PVARP within a multi-site pacing system.

TABLE 1

| Patent Number | Inventors | Title |
| --- | --- | --- |
| 3,937,226 | Funke | Arrhythmia Prevention Apparatus |
| 4,088,140 | Rockland et al. | Demand Anti-Arrhythmia Pacemaker |
| 4,354,497 | Kahn | Cardiac Depolarization Detection Apparatus |
| 4,928,688 | Mower | Method and Apparatus of Treating Hemodynamic Dysfunction |
| 5,388,586 | Lee et al. | Methods and Apparatus for Sensing Intracardiac Signals for an Implantable Cardiac Pacemaker |
| 5,683,429 | Mehra | Method and Apparatus for Cardiac Pacing to Prevent Atrial Fibrillation |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to cardiac pacing in general, and facilitate the use of the PVC response feature in biventricular sensing configurations, in particular. Such problems include, for example, having to disable the PVC response function in biventricular pacing systems. Specifically, previous biventricular pacing systems have had to be programmed so as to disable the initiation of an extended PVARP that would otherwise occur in response to a detected PVC. Other problems include the possibility of allowing pacemaker mediated tachycardia to occur in biventricular pacing systems having the PVC response function disabled in order to avoid extended ventricular sensing.

Various embodiments of the present invention have the object of solving at least one of the foregoing problems. While some biventricular pacing systems have been able to prevent extended ventricular sensing, they have required that the PVC response function be disabled. Thus, these prior biventricular pacing systems have only been able to deal with one problem or the other, and not both. Thus, one condition always remains as a possibility. It is therefore another object of the present invention to provide an improved apparatus and methodology for allowing a biventricular pacing system to appropriately respond to detected PVC's with the appropriate PVC response while also preventing extended ventricular sensing from occurring in a problematic context.

In comparison to known implementations of cardiac pacing systems and methodologies, various embodiments of the present invention may provide one or more of the following advantages: allowing the use of the PVC response feature on biventricular and biatrio pacing system and preventing extended ventricular sensing from occurring while the PVC response feature is enabled.

Some embodiments of the invention include one or more of the following features: a mechanism that works in conjunction with the extended PVARP function so that both extended ventricular sensing and pacemaker mediated tachycardia are prevented. For example, the present invention triggers a programmable ventricular blanking period in conjunction with the extended PVARP to accomplish this object.

Another feature of the present invention is a pacing system that accommodates the dual sensing of the same ventricular event by a biventricular pacing system. For example, the present invention provides a programmable ventricular blanking period to generally coincide with a measured inter-ventricular conduction delay so as to account for this dual sensing.

Yet another feature of the present invention is a pacing system having an algorithm that allows a PVC response to properly function in the context of a biatrio-biventricular pacing system. (Bi)atrio-biventricular is meant to include a biventricular system that may include a biatrial component or may only pace/sense a single atrial chamber.

In a biventricular system, a first ventricular lead is placed in the right ventricle and a second ventricular lead is placed in the left ventricle. Thus, each ventricular event will typically be sensed twice by the pacing system as the cardiac depolarization wave moves around the heart. More specifically, one of the ventricular leads will first sense the event (designated R1) and at some time interval later (generally >100 ms), the other ventricular lead will then separately sense the same event (designated R2).

In the context of a PVC response, each repetitive sense of the ventricular event will restart the extended PVARP. As such, the predetermined time period of the extended PVARP is effectively increased by an amount of time equal to the inter-ventricular conduction delay (IVCD). The IVCD is essentially the time delay between R1 and R2. Naturally occurring P waves will not be sensed during this extended time period and consequently, any intrinsic AV conduction will allow spontaneous R waves to occur which will be falsely classified as a PVC. This leads to a repetitive cycling where therapy to the patient is lost until the atrial rate slows down.

Thus, another feature of the present invention may be a programmable ventricular blanking period (VBP) that is initiated when the extended PVARP is initiated. The programmable VBP exceeds the IVCD so that repetitive sensing of the same ventricular event will not restart the extended PVARP. Because the extended PVARP is not reset, it functions as intended and the repetitive cycling described above is avoided. In this manner, therapy is consistently delivered to the patient without interruption due to extended ventricular sensing.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 6 is an electrocardiogram illustrating the response of a biventricular pacing system to a PVC in a patient with Intrinsic AV Conduction and Left Bundle Branch Block (LBBB).

FIG. 7 is a combined atrio-ventricular electrogram (in phase with FIG. 6) illustrating the response of a biventricular pacing system to a PVC.

DETAILED DESCRIPTION

In the following detailed description of the preferred embodiments, reference is made to the accompanying drawings that form a part hereof, and in which are shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
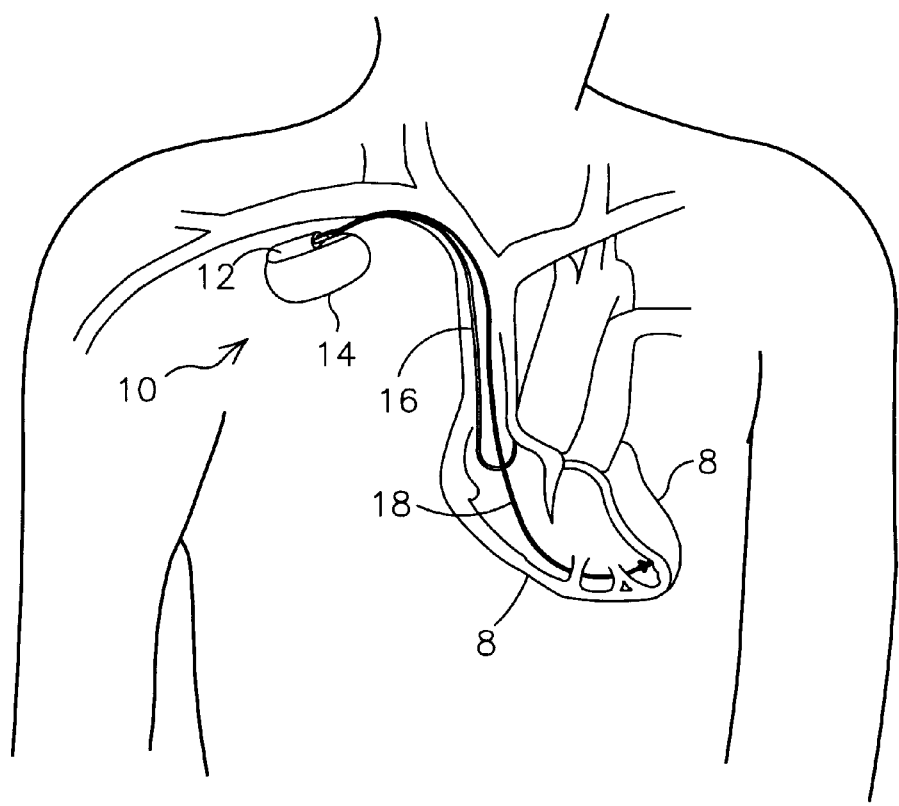
FIG. 1 is a schematic illustration of an implantable medical device within the chest cavity of a patient, adjacent to the patient's heart.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to connector module 12 of hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
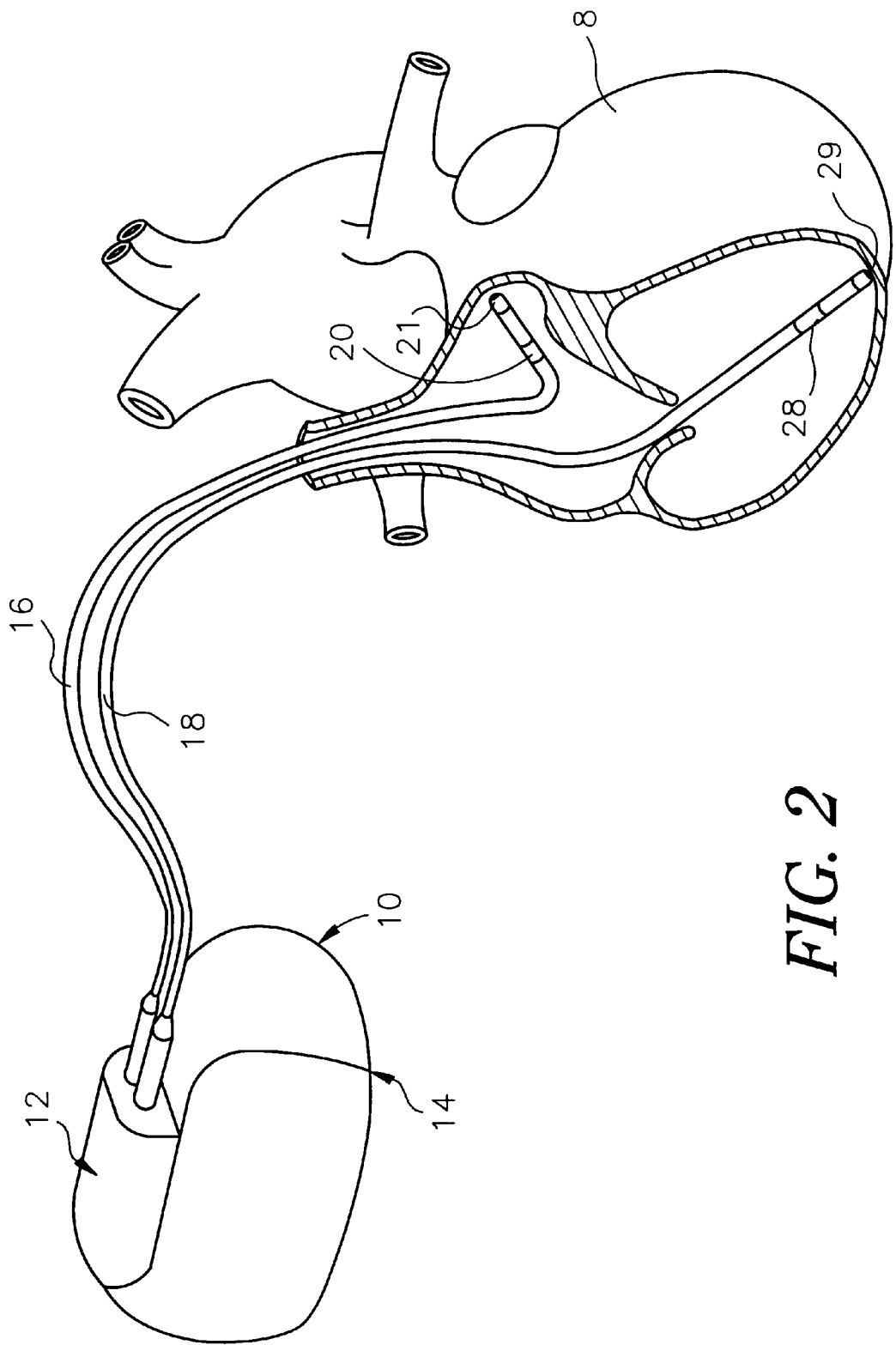
FIG. 2 is a partially sectional perspective view of an implantable medical device coupled to a mammalian heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
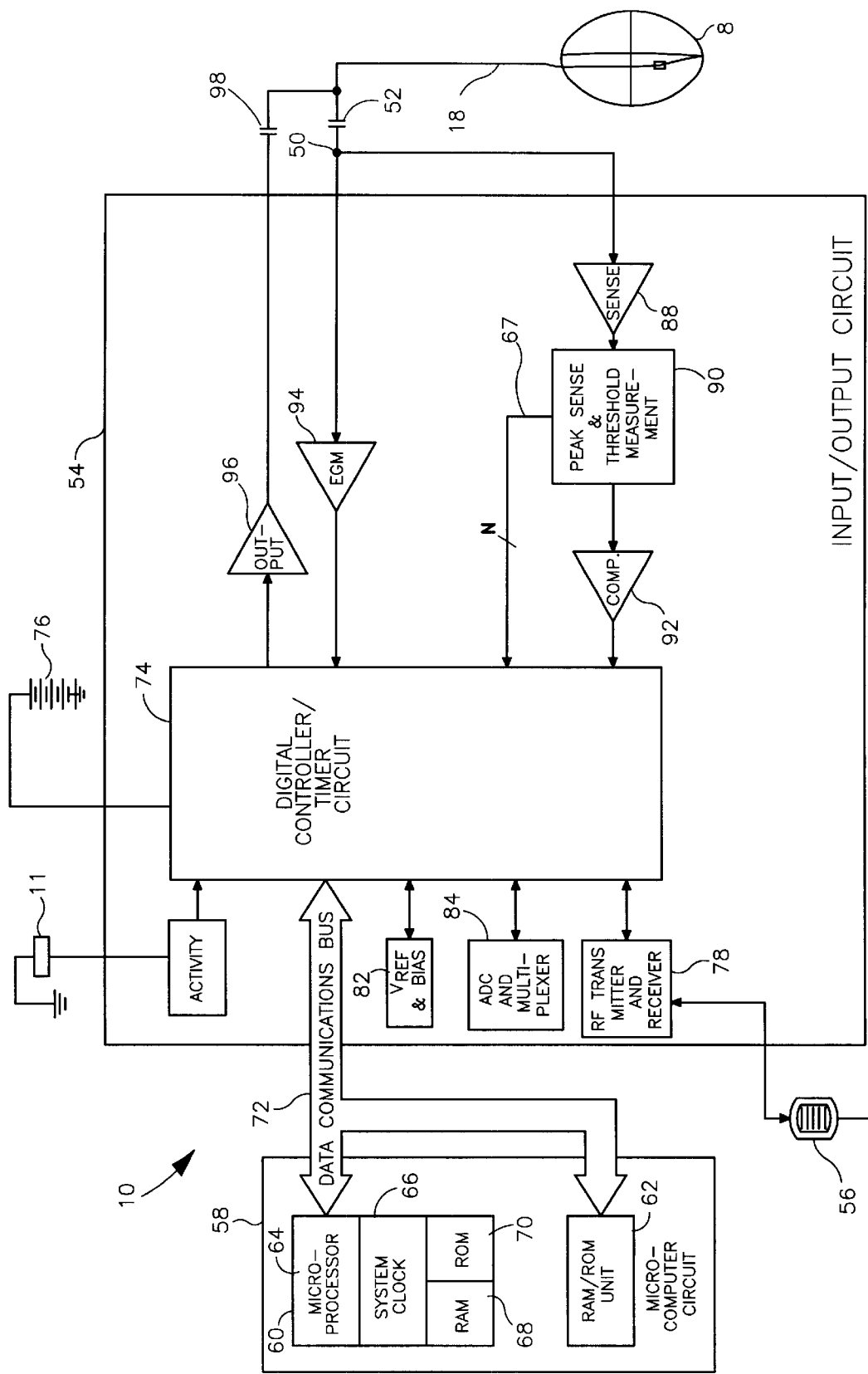
FIG. 3 is a block diagram illustrating the constituent components of an implantable medical device.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing with heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
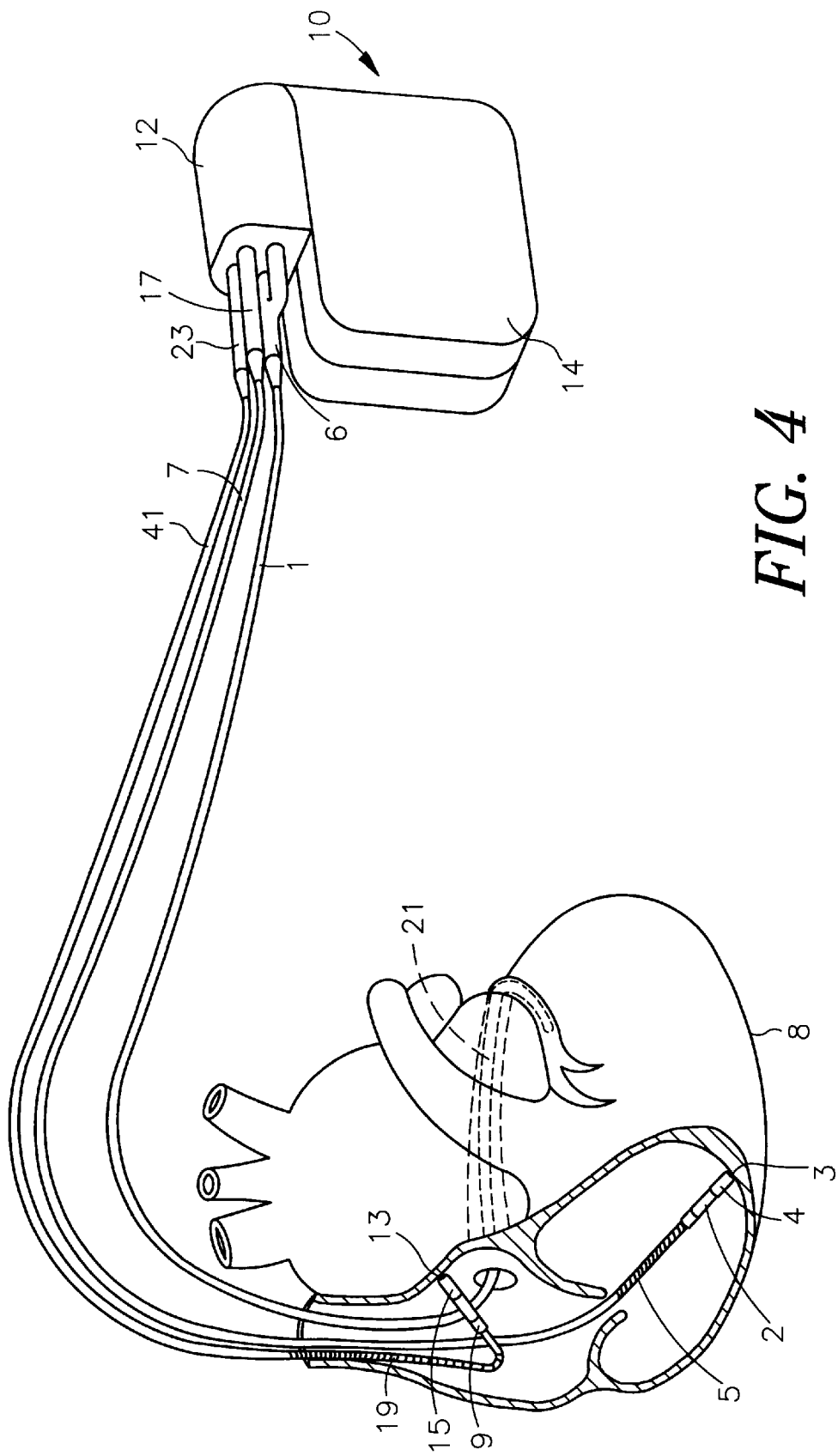
FIG. 4 is a partially sectional perspective view of a multi-lead, multi-chamber implantable medical device.
Figure 5:
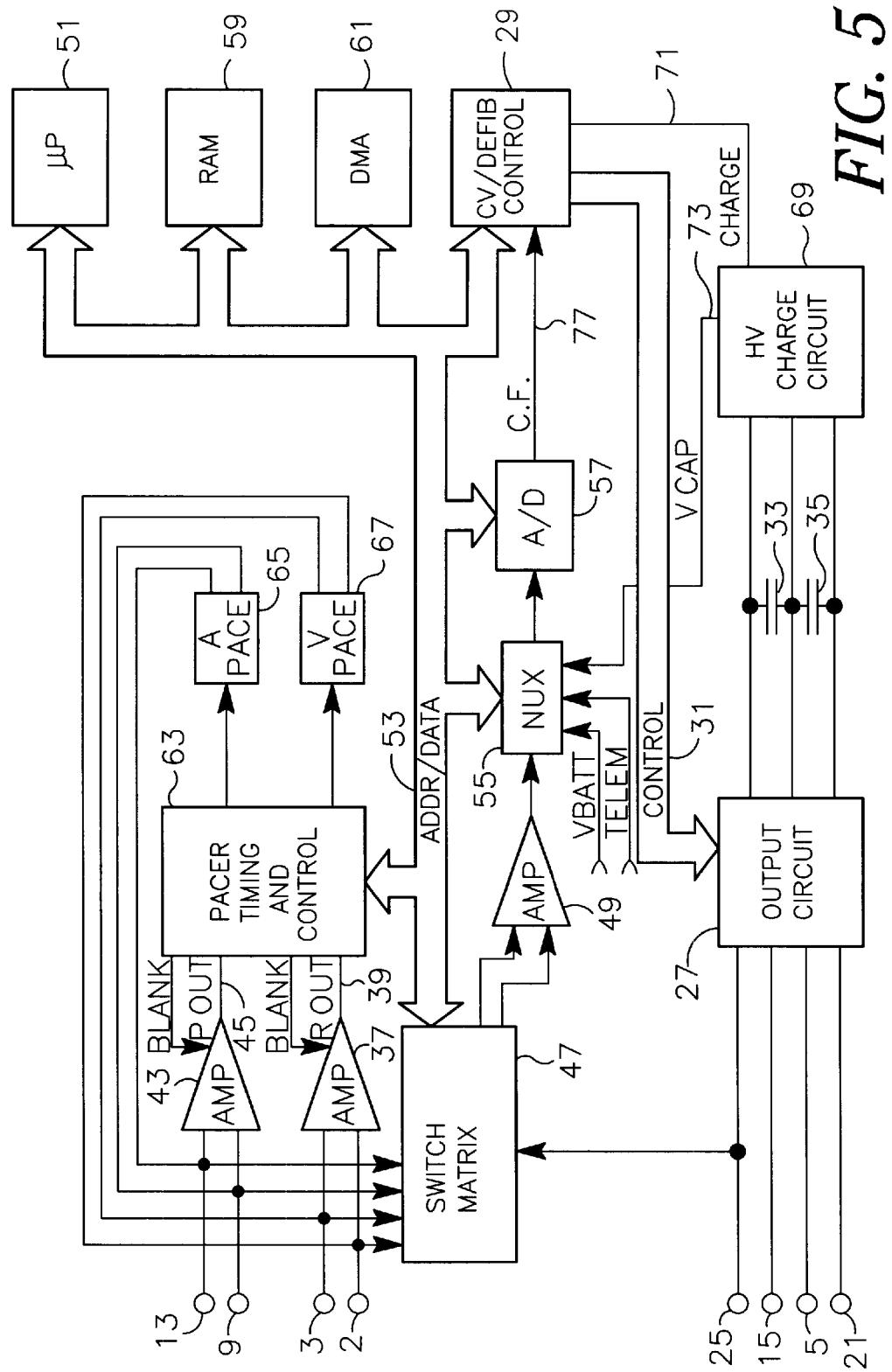
FIG. 5 is a block diagram of the constituent components of the multi-lead, multi-chamber implantable medical device.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

IMD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No.

5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

FIGS. 6 and 7 illustrate a PVC (Premature Ventricular Contraction) response with a biventricular pacing system when the PVC response function is enabled. FIG. 6 is an electrocardiogram (ECG) and FIG. 7 is a corresponding electrogram (EGM), representing the signals identified by IMD 10. An atrial sense (AS) occurs at event 100. After a preset and predetermined delay, an appropriate biventricular pacing complex 110 (BiVP) is generated. A T wave is present on the ECG as event 115.

Event 120 in FIG. 6 represents an actual PVC. This single PVC is sensed twice by IMD 10 as event 122 and event 124, as shown in FIG. 7. This double sensing occurs because a lead present in the left ventricle senses event 122 as R1 while another lead present in the right ventricle senses event 124 as R2 some time later. R1 and R2 occur at different times as the signal propagates (in this example) from the left ventricle to the right ventricle of heart 8. The time or delay between R1 and R2 is the inter-ventricular conduction delay (IVCD) 200, which is typically in the range of 80–180 ms. In this case, IVCD 200 is illustrated as being about 130 ms.

As soon as R1 is detected by IMD 10, the algorithms performed within microcomputer circuit 58 initiate a first extended PVARP 205. The extended PVARP 205 (post ventricular atrial refractory period) is a blanking interval, during which atrial events are not acknowledged. This period is typically set at 400 ms, though it may range from about 350 ms to 450 ms. The initiation of an extended PVARP is a precautionary step to prevent recognizing retrograde P waves (which would normally occur during PVARP, if at all) as legitimate atrial events. The occurrence of pacemaker mediated tachycardia (PMT) can be reduced by utilizing the extended PVARP. Simultaneously, the lower rate timer 210 is also initiated with the initiation of the extended PVARP 200 of 400 ms, in this example.

After the IVCD 200 has ended, the right ventricular lead senses R2. Since this is a ventricular event without a preceding atrial event, it is classified as a PVC. As such, a second extended PVARP 215 of 400 ms is initiated and the lower rate timer is reset at 220.

During the overlap between the first extended PVARP 205 and the second extended PVARP 215, a legitimate atrial event 130 occurs. That is, a P wave is generated. However, as intended, atrial events are not recognized during this blanking period. Subsequently, event 135 occurs which is a proper intrinsic atrio-ventricular conducted beat. However, because atrial event 130 was in effect not sensed, IMD 10 recognizes event 135 as another PVC. The lead within the right ventricle senses event 138 and a first extended PVARP of 400 ms is initiated. After the expiration of the IVCD 200 (130 ms) the lead within the left ventricle also senses event 135, but recognizes it as a separate event 140. Again, there is no intervening atrial event, thus it is classified as a PVC. A second extended PVARP 230 of 400 ms is initiated.

An atrial event 145 occurs after some period of time. Because heart 8 has returned to an intrinsic beat, atrial event 145 should be recognized by IMD 10. If IMD 10 only utilized a single ventricular lead, atrial event 145 would have been properly recognized because it falls outside of the blanking interval defined by the first extended PVARP 225 of 400 ms. However, because a second ventricular lead was utilized, the same event 135 caused the second extended PVARP 230 of 400 ms to occur. This effectively extended the blanking interval to the time predefined for extended PVARP plus the time of the IVCD, for a total of about 530 ms, in this case. This longer blanking period prevents the atrial event 145 from being properly recognized.

As such, when another intrinsic conducted beat 150 occurs, it is again incorrectly recognized as a PVC by IMD 10. This process repeats itself in a cyclic manner until the atrial rate slows sufficiently to break the cycle and is referred to as extended ventricular sensing. While this process is cycling, therapy for the patient is lost.

Figure 8:
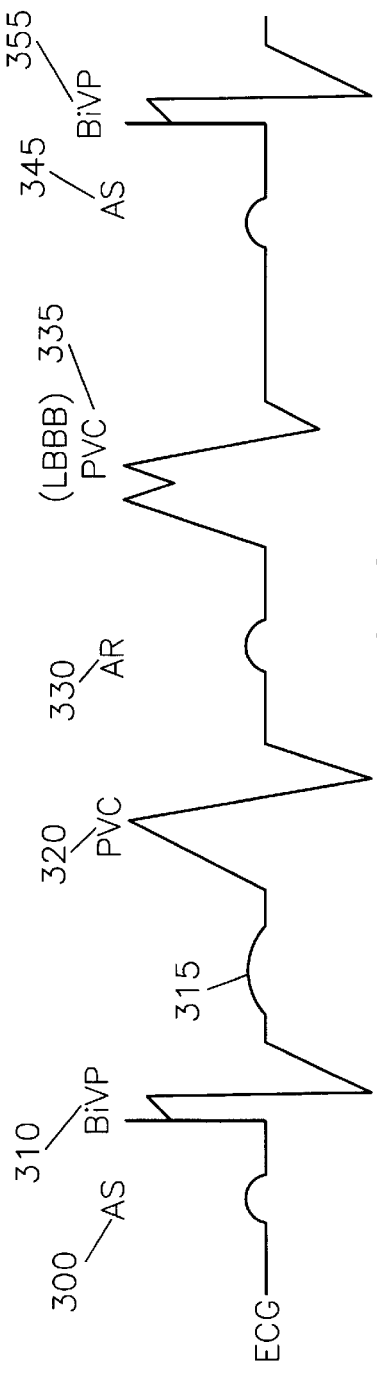
FIG. 8 is an electrocardiogram illustrating the response of a biventricular pacing system incorporating a programmable Ventricular Blanking Period to a PVC.
Figure 9:
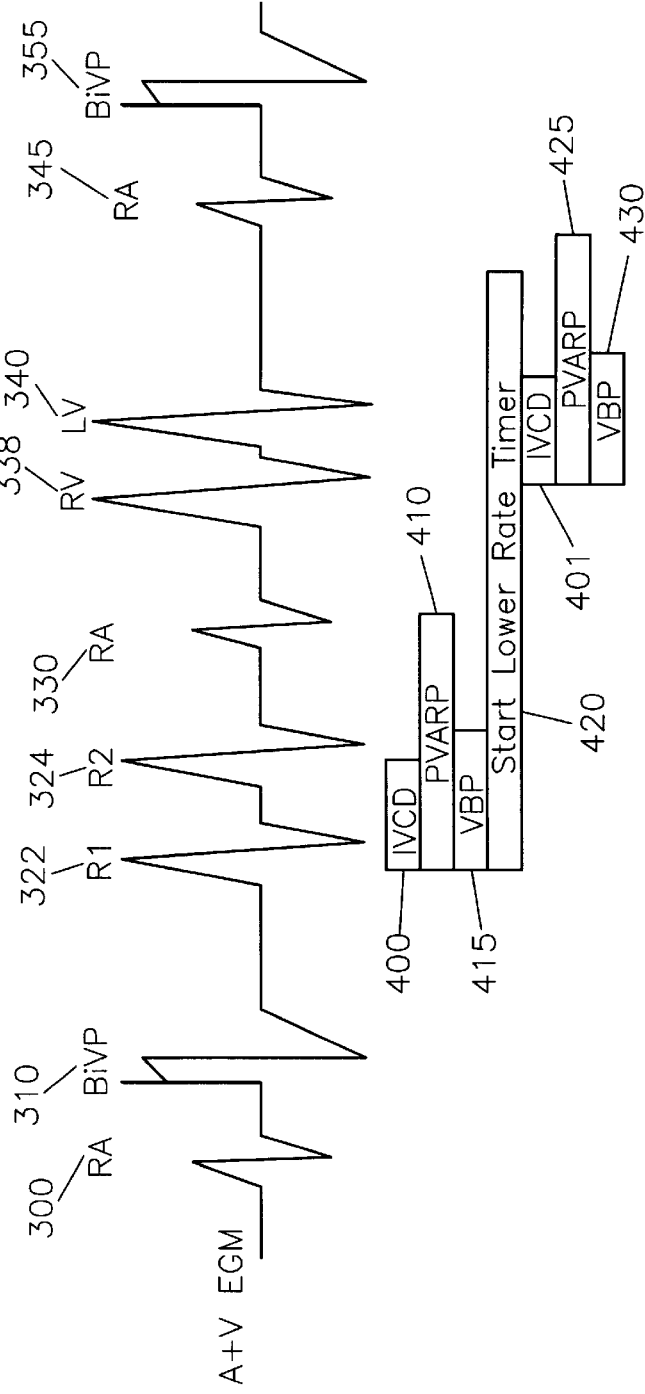
FIG. 9 is an electrogram (in phase with FIG. 8) illustrating the response of a biventricular pacing system incorporating a programmable Ventricular Blanking Period to a PVC.

FIGS. 8 and 9 illustrate a PVC response with the biventricular pacing system of the present invention, when the PVC response function is enabled. FIG. 8 is an electrocardiogram (ECG) and FIG. 9 is a corresponding electrogram (EGM), representing the signals identified by IMD 10.

IMD 10 senses an atrial event at event 300. A predetermined amount of time later, a biventricular pacing complex is properly generated as event 310. At event 315 a T wave is propagated. At event 320, a ventricular event is sensed. Since no atrial event preceded it, event 320 is (properly) classified as a PVC. In this case, left ventricular lead first senses the PVC as R1 event 322. As such, according to the previously discussed PVC response parameters an extended PVARP 410 of 400 ms is initiated.

At this point, the programmed ventricular blanking period (VBP) 415 is also initiated. During VBP 415, ventricular events are no longer recognized by IMD 10. Hence, they are effectively blanked out. VBP coincides with but is shorter than extended PVARP 410. Thus, for a period of time when the two overlap, both atrial and ventricular events are effectively blanked via the extended PVARP, and programmed VBP respectively.

VBP 415 prevents the triggering of a second extended PVARP of 400 ms. As explained above, without VBP 415, a second extended PVARP would have been triggered by the detection of R2 at event 324. However, since ventricular signals are blanked during VBP 415, only PVARP 410 is initiated. At the same time, lower rate timer 420 is also initiated.

VBP 415 is set for a predetermined period of time. At a minimum, VBP must cover the IVCD in order to prevent the second ventricular lead from triggering a PVARP based on the same event that triggered the first ventricular lead. That is, the VBP 415 needs to be long enough so that R2 is ignored. VBP should not extend too far beyond the IVCD so that subsequent genuine PVC's are also ignored.

VBP 415 will initially be set by measuring the IVCD in a given patient. In order to account for the natural fluctuations in this time period that occur with each heartbeat, the VBP will be set to the measured IVCD plus a margin of error. A margin of error of about 10–30% of the IVCD provides a satisfactory result. Thus, the VBP becomes the measured IVCD+10–30% of the IVCD. The initial measurements of the IVCD can be made by a cardiologist and used to preprogram (or reprogram) IMD 10. Alternatively, IMD 10 can either initially determine or periodically sense the patient's IVCD and then use that data to set the VBP. Thus, in this case the IVCD is about 130 ms so VBP 415 will be about 143 ms (130 ms+10%).

A refractory atrial event occurs as event 330. This event occurs after VBP 415 has expired (i.e., after 143 ms), but while PVARP 410 is continuing and it is accordingly blanked. An intrinsic conducted beat occurs at event 335. Since atrial event 330 was not recognized as such, event 335 is classified as a PVC. This determination is made as right ventricular lead senses the beat (RV) as event 338. It is at this point that an extended PVARP 425 of 400 ms is initiated and programmed VBP 430 of 143 ms is also initiated. As the intrinsic beat is conducted through the left ventricle (as event 340), it is blanked because it occurs within the programmed VBP 430. Thus, a second extended PVARP is avoided.

IMD 10 senses an atrial event as event 345. It is important to note the timing of this event. That is, if a second extended PVARP had been initiated after IVCD 401, atrial event 345 would not have been sensed. However, by incorporating the programmed VBP 430, this situation is effectively avoided. As such, a properly generated biventricular pacing complex is generated by IMD 10 and therapy is restored to the patient.

Figure 10:
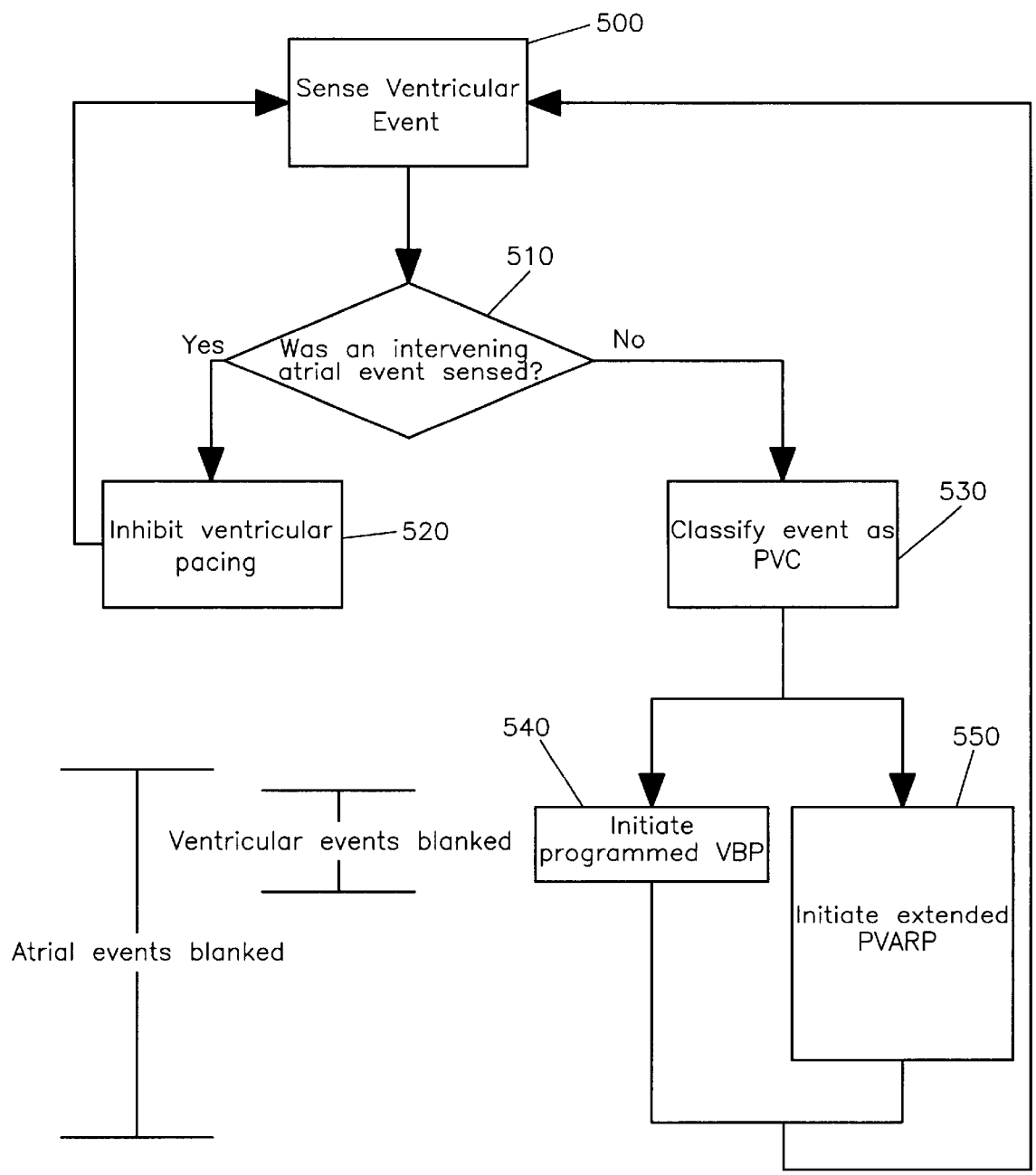
FIG. 10 is a flow diagram illustrating the processing of ventricular events by a biventricular pacing system incorporating a programmable Ventricular Blanking Period.

In this manner, the PVC response feature can be effectively employed within a biventricular IMD 10 while still effectively preventing PMT. FIG. 10 is a flow diagram illustrating a sensing process of biventricular IMD 10 incorporating a VBP with a PVC response. At step 500, IMD 10 senses a ventricular event. At step 510, it is determined whether an intervening atrial event occurred. If yes, the process proceeds to step 520, where ventricular pacing is inhibited and the system returns to step 500. If, at step 510, an intervening atrial event was not sensed, the process proceeds to step 530.

As step 530, the ventricular sensed event is classified as a PVC and the preprogrammed PVC response is initiated. That response includes initiating the programmed VBP at step 540 and simultaneously initiating the extended PVARP at step 550. As explained above, during the period of overlap between the extended PVARP and the programmed VBP, neither ventricular nor atrial events are sensed and any such event occurring is essentially blanked by IMD 10. The VBP concludes first. Thus, for the remainder of the extended PVARP, subsequently occurring ventricular events can reinitiate a PVC response. Finally, it is only after the conclusion of the extended PVARP that atrial events will be sensed as such. Thus, after steps 540 and 550, the process returns to step 500. In order for an intervening atrial event to have been sensed as required at step 510 (after returning from step 550), that atrial event must have occurred after the cessation of the extended PVARP at step 550.

The preceding specific embodiments are illustrative of the practice of the invention. It is to be understood, therefore, that other expedients known to those skilled in the art or disclosed herein may be employed without departing from the invention or the scope of the claims. For example, the present invention is not limited to biventricular pacing systems, Biatrial pacing systems, or dual chamber pacing systems. Rather, the present invention can be employed in any pacing system wherein a programmable Ventricular Blanking Period can aid in the prevention or limit the furtherance of negative cardiac conditions or negative pacing system performance. The present invention further includes within its scope methods of making and using the pacing system incorporating the programmable VBP described hereinabove.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An implantable cardiac pacemaker, comprising:
    a first ventricular lead;
    a second ventricular lead; and
    a controller that controls the implantable cardiac pacemaker based in part on signals received from the first and second ventricular leads, and initiates an extended post ventricular atrial refractory period of between about 350–450 ms, during which sensed atrial events are ignored, and a programmable ventricular blanking period in response to a premature ventricular contraction.

2. The cardiac pacemaker of claim 1, wherein the post ventricular atrial refractory period is approximately equal to 400 ms.

3. The implantable cardiac pacemaker of claim 1, wherein the controller includes a microprocessor coupled to the first and second ventricular leads to sense the signals, and a microcomputer circuit coupled to the microprocessor that stores an algorithm that defines control parameters for the microprocessor, the control parameters controlling the response of the microprocessor to the premature ventricular contraction.

4. The implantable cardiac pacemaker of claim 1, wherein the ventricular blanking period has a length of time that corresponds to a length of time defined by an interventricular conduction delay.

5. The implantable cardiac pacemaker of claim 1, wherein the ventricular blanking period has a length of time that is approximately equal to a length of time defined by an interventricular conduction delay.

6. The implantable cardiac pacemaker of claim 5, wherein the interventricular conduction delay is between about 80–180 ms.

7. The implantable cardiac pacemaker of claim 1, wherein the ventricular blanking period has a length of time that is approximately equal to a length of time defined by an interventricular conduction delay plus a margin of error.

8. The implantable cardiac pacemaker of 7, wherein the margin of error is equal to approximately 10–30% of the interventricular conduction delay.

9. The implantable cardiac pacemaker of claim 1, wherein the response initiates the extended post ventricular atrial refractory period and the programmed ventricular blanking period simultaneously.

10. An implantable medical device, comprising;
biventricular pacing and sensing leads; and
a programmable cardiac pacing system coupled to the biventricular pacing and sensing leads, and having a preprogrammed premature ventricular contraction response function that initiates an extended post ventricular atrial refractory period for a first predetermined period of time of between about 350–450 ms, during which sensed atrial events are ignored, and initiates a programmed ventricular blanking period for a second predetermined period of time, following the detection of a premature ventricular contraction.

11. The cardiac pacemaker of claim 10, wherein the post ventricular atrial refractory period is approximately equal to 400 ms.

12. The implantable medical device of claim 10, wherein the pacing system will not restart the extended post ventricular atrial refractory period in response to ventricular events occurring during the programmed ventricular blanking period.

13. The implantable medical device of claim 10, wherein the extended post ventricular atrial refractory period and the programmed ventricular blanking period are initiated simultaneously.

14. The implantable medical device of claim 10, wherein the first predetermined period of time is longer than the second predetermined period of time.

15. The implantable medical device of claim 10, wherein the second predetermined period of time is approximately equal to an interventricular conduction delay.

16. The implantable medical device of claim 15, wherein the interventricular conduction delay is between about 80–180 ms.

17. The implantable medical device of claim 10, wherein the second predetermined period of time is approximately equal to an interventricular conduction delay plus a predetermined margin of error.

18. The implantable medical device of claim 17, wherein the margin of error is approximately 10–30% of the interventricular conduction delay.

19. The implantable medical device of claim 10, wherein the programmed ventricular blanking period prevents the double sensing of a single premature ventricular contraction.

20. The implantable medical device of claim 10, wherein a second extended post ventricular atrial refractory period will be initiated upon the determination that a subsequent premature ventricular contraction has occurred after the programmed ventricular blanking period terminates.

21. The implantable medical device of claim 10, wherein the second predetermined period of time is determined and programmed based on a measured interventricular conduction delay.

22. The implantable medical device of claim 21, wherein the interventricular conduction delay is measured prior to implanting the implantable medical device.

23. The implantable medical device of claim 21, wherein the interventricular conduction delay is measured after implanting the implantable medical device.

24. The implantable medical device of claim 21, wherein the second predetermined period of time is programmed to be approximately equal to the measured interventricular conduction delay.

25. The implantable medical device of claim 21, wherein the second predetermined period of time is programmed to be approximately equal to the measured interventricular conduction delay plus a predetermined margin of error.

26. The implantable medical device of claim 21, wherein the second predetermined period of time is programmed to be approximately equal to the measured interventricular conduction delay plus a predetermined margin of error.

27. The implantable medical device of claim 26, wherein the margin of error is equal to about 10–30% of the measured interventricular conduction delay.

28. The implantable medical device of claim 10, wherein the second predetermined period of time is set by a measurement made by the cardiac pacing system through the biventricular pacing and sensing leads, of an interventricular conduction delay.

29. A method of preventing pacemaker mediated tachycardia in a biventricular cardiac pacing system, the method comprising:
detecting a premature ventricular contraction;
initiating an extended post ventricular atrial refractory period of between about 350–450 ms during which atrial events are not sensed by the cardiac pacing system; and
initiating a programmable ventricular blanking period, during which ventricular events are not sensed by the cardiac pacing system.

30. The method of claim 29, wherein the extended post ventricular atrial refractory period and the programmed ventricular blanking period are initiated simultaneously.

31. The method of claim 29, further comprising:
terminating the programmed ventricular blanking period after the expiration of a first time period; and
terminating the extended post ventricular atrial refractory period after the expiration of a second time period, wherein the second time period is longer than the first time period.

32. The method of claim 31, further comprising:
setting the first time period to be approximately equal to an interventricular conduction delay.

33. The method of claim 31, further comprising:
setting the first time period to be approximately equal to an interventricular conduction delay plus a margin of error.

34. The method of claim 33, wherein the margin of error is approximately 10–30% of the interventricular conduction delay.

35. The method of claim 31, further comprising:
measuring an interventricular conduction delay; and programming the cardiac pacing system to set the first time period based on the measured interventricular conduction delay.

36. The method of claim 35, wherein the first time period is set to be approximately equal to the interventricular conduction delay.

37. The method of claim 35, wherein the first time period is set to be approximately equal to the interventricular conduction delay plus a margin of error.

38. The method of claim 37, wherein margin of error is approximately 10–30% of the interventricular conduction delay.

39. A method of utilizing a biventricular cardiac pacing system, the method comprising:

providing a first ventricular lead and a second ventricular lead;

sensing atrial and ventricular events;

classifying a sensed ventricular event following another ventricular event without an intervening atrial event as a premature ventricular contraction;

initiating a first time period, during which atrial events are blanked out by the cardiac pacing system so that pacemaker mediated tachycardia is avoided; and initiating a second time period, during which ventricular events are blanked out by the cardiac pacing system, wherein the second time period is at least as long as an interventricular conduction delay so that an event sensed by the first ventricular lead and classified as the premature ventricular contraction is not subsequently classified as another premature ventricular contraction when sensed by the second ventricular lead, so that an extended ventricular sensing cycle is avoided.

40. The method of claim 39, further comprising:

measuring the interventricular conduction delay; and setting the second time period based on the measured interventricular conduction delay.

41. The method of claim 40, further comprising:

adding a margin of error to the second time period.

42. The method of claim 41, wherein the margin of error is equal to (10–30%) of the measured interventricular conduction delay.

43. An implantable programmable biventricular cardiac pacing system, comprising:

an atrial lead;

a first ventricular lead;

a second ventricular lead;

a microprocessor coupled to the atrial lead and the first and second ventricular leads, the microprocessor being configured to monitor sensed ventricular and atrial events so that a ventricular event sensed after another ventricular event without an intervening atrial sense is determined to be a premature ventricular contraction; and a programmable microcomputer circuit coupled to the microprocessor and including an algorithm for responding to a determined premature ventricular contraction by initiating an extended post ventricular atrial refractory period, during which atrial events are blanked for a period of between about 350–450 ms, and initiating a programmable ventricular blanking period having a duration equal to a measured value of an interventricular conduction delay plus a margin of error equal to about 10–30% of the interventricular conduction delay, during which ventricular events sensed by the first or the second ventricular lead are ignored so that both pacemaker mediated tachycardia and extended ventricular sensing are avoided by the cardiac pacing system.

44. An implantable cardiac pacemaker, comprising:

means for sensing biventricular events; and means for controlling the implantable cardiac pacemaker based in part on signals received from the means for sensing biventricular events, and initiating an extended post ventricular atrial refractory period of between about 350–450 ms, during which sensed atrial events are ignored, and a programmable ventricular blanking period in response to a premature ventricular contraction.

45. The implantable cardiac pacemaker of claim 44, wherein the post ventricular atrial refractory period is approximately equal to 400 ms.

46. The implantable cardiac pacemaker of claim 44, wherein the ventricular blanking period has a length of time that corresponds to a length of time defined by an interventricular conduction delay.

47. The implantable cardiac pacemaker of claim 44, wherein the ventricular blanking period has a length of time that is approximately equal to a length of time defined by an interventricular conduction delay.

48. The implantable cardiac pacemaker of claim 47, wherein the interventricular conduction delay is between about 80–180 ms.

49. The implantable cardiac pacemaker of claim 44, wherein the ventricular blanking period has a length of time that is approximately equal to a length of time defined by an interventricular conduction delay plus a margin of error.

50. The implantable cardiac pacemaker of claim 49, wherein the margin of error is equal to approximately 10–30% of the interventricular conduction delay.

51. The implantable cardiac pacemaker of claim 44, wherein the response initiates the extended post ventricular atrial refractory period and the programmed ventricular blanking period simultaneously.

52. A biventricular cardiac pacing system configured to prevent pacemaker mediated tachycardia, comprising:

means for detecting a premature ventricular contraction;

means for initiating an extended post ventricular atrial refractory period of between about 350–450 ms during which atrial events are not sensed by the cardiac pacing system; and means for initiating a programmable ventricular blanking period, during which ventricular events are not sensed by the cardiac pacing system.

53. The cardiac pacing system of claim 52, wherein the extended post ventricular atrial refractory period and the programmed ventricular blanking period are initiated simultaneously.

54. The cardiac pacing system of claim 52, further comprising:

means for terminating the programmed ventricular blanking period after the expiration of a first time period; and means for terminating the extended post ventricular atrial refractory period after the expiration of a second time period, wherein the second time period is longer than the first time period.

55. The cardiac pacing system of claim 54, wherein the first time period is approximately equal to an interventricular conduction delay.

56. The cardiac pacing system of claim 54, further comprising:

means for setting the first time period to be approximately equal to an interventricular conduction delay plus a margin of error.

57. The cardiac pacing system of claim 56, wherein the margin of error is approximately 10–30% of the interventricular conduction delay.

58. The cardiac pacing system of claim 54, further comprising:
   means for measuring an interventricular conduction delay; and
   means for programming the cardiac pacing system to set the first time period based on the measured interventricular conduction delay.

59. The cardiac pacing system of claim 58, wherein the first time period is approximately equal to the interventricular conduction delay.

60. The cardiac pacing system of claim 58, wherein the first time period is approximately equal to the interventricular conduction delay plus a margin of error.

61. The cardiac pacing system of claim 60, wherein the margin of error is approximately 10–30% of the interventricular conduction delay.

62. A biventricular cardiac pacing system, comprising:
   means for sensing atrial and biventricular events;
   means for classifying a sensed ventricular event following another ventricular event without an intervening atrial event as a premature ventricular contraction;
   means for initiating a first time period, during which atrial events are blanked out by the cardiac pacing system so that pacemaker mediated tachycardia is avoided; and
   means for initiating a second time period, during which ventricular events are blanked out by the cardiac pacing system, wherein the second time period is at least as long as an interventricular conduction delay so that an event sensed by the first ventricular lead and classified as the premature ventricular contraction is not subsequently classified as another premature ventricular contraction when sensed by the second ventricular lead, so that an extended ventricular sensing cycle is avoided.

63. The cardiac pacing system of claim 62, further comprising:
   means for measuring the interventricular conduction delay; and
   means for setting the second time period based on the measured interventricular conduction delay.

64. The cardiac pacing system of claim 63, wherein a margin of error is added to the second time period.

65. The cardiac pacing system of claim 64, where in the margin of error is equal to (10–30%) of the measured interventricular conduction delay.

* * * * *